(12) United States Patent  
Lin et al.

(10) Patent No.: US 11,492,581 B2
(45) Date of Patent: Nov. 8, 2022

(54) MICROWELL DEVICE AND METHOD OF MANUFACTURING THE SAME

(71) Applicant: Academia Sinica, Taipei (TW)

(72) Inventors: Keng-Hui Lin, New Taipei (TW); Cheng-Kuang Huang, Hsinchu (TW)

(73) Assignee: ACADEMIA SINICA, Taipei (TW)

( * ) Notice: Subject to any disclaimer, the term of this patent is extended or adjusted under 35 U.S.C. 154(b) by 219 days.

(21) Appl. No.: 16/838,901

(22) Filed: Apr. 2, 2020

(65) Prior Publication Data

US 2020/0332239 A1    Oct. 22, 2020

Related U.S. Application Data

(60) Provisional application No. 62/835,009, filed on Apr. 17, 2019.

(51) Int. Cl.
| | | |
|---|---|---|
| C12M 1/32 | (2006.01) | |
| C12M 1/00 | (2006.01) | |
| B01L 3/00 | (2006.01) | |
| C12N 5/00 | (2006.01) | |

(52) U.S. Cl.
CPC .......... *C12M 23/12* (2013.01); *B01L 3/5085* (2013.01); *C12M 23/20* (2013.01); *C12M 23/38* (2013.01); *B01L 2200/12* (2013.01); *B01L 2300/0819* (2013.01); *B01L 2300/0829* (2013.01); *B01L 2300/0858* (2013.01); *C12N 5/0062* (2013.01)

(58) Field of Classification Search
CPC ...... C12M 23/12; C12M 23/20; C12M 23/38; B01L 3/5085; B01L 2200/12; B01L 2300/0819; B01L 2300/0829; B01L 2300/0858; C12N 5/0062

See application file for complete search history.

(56) References Cited

U.S. PATENT DOCUMENTS

| | | | | |
|---|---|---|---|---|
| 2003/0180191 A1* | 9/2003 | Suzuki | ............. | B29C 66/73921 422/400 |
| 2003/0228706 A1* | 12/2003 | Ramstad | .......... | G01N 33/54313 436/178 |
| 2005/0142033 A1* | 6/2005 | Glezer | ................... | G01N 21/66 422/400 |
| 2010/0012413 A1* | 1/2010 | Chaney | ................... | B60H 1/30 180/165 |
| 2010/0022416 A1* | 1/2010 | Flemming | ............. | B01L 3/5085 506/39 |
| 2014/0273191 A1 | 9/2014 | Tipgunlakant et al. | | |

FOREIGN PATENT DOCUMENTS

| | | |
|---|---|---|
| CN | 103282481 A | 9/2013 |
| CN | 109016275 A | 12/2018 |
| CN | 109337814 A | 2/2019 |
| WO | 2017135153 A1 | 8/2017 |
| WO | 2018061846 A1 | 4/2018 |

\* cited by examiner

*Primary Examiner* — Michael L Hobbs
(74) *Attorney, Agent, or Firm* — Li & Cai Intellectual Property (USA) Office (57) ABSTRACT

A microwell device and a method of manufacturing the same are provided. The microwell device includes a substrate and a plurality of microwells formed on the substrate. In addition, each of the microwells includes a cavity being recessed on the substrate and an opening, and the diameter of the opening is smaller than the largest inner diameter of the cavity. Furthermore, the microwells are curved.

18 Claims, 12 Drawing Sheets

MICROWELL DEVICE AND METHOD OF MANUFACTURING THE SAME

CROSS-REFERENCE TO RELATED PATENT APPLICATION

This application claims priority from the U.S. Provisional Patent Application Ser. No. 62/835,009 filed Apr. 17, 2019, which application is incorporated herein by reference in its entirety.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a cell culture device, and more particularly to a microwell device and a method of manufacturing the same.

BACKGROUND OF THE DISCLOSURE

In the past, scientists have used two-dimensional (2D) cell culture to observe and operate cells to build knowledge of cellular biology. With the advancement of technology, scientists have found that, in 3D cell culture, the cell morphogenesis and migration, cell survival rate, gene expression, organoid formation, cell differentiation, and virulence tolerance are all different from those in 2D cell culture, and compared with 2D cell culture, 3D cell culture can better reflect the growth environment of cells in vivo. Therefore, scientists have begun using 3D cell culture, such as gel-embedded culture, prefabricated scaffolds, or hanging-drop culture and so on to replace 2D cell culture.

The shape of most 3D cell culture microwells is cylindrical, which is still a little different from the growth environment of cells in vivo. Some 3D cell culture are hemi-spherical which may be achieve a better effect than cylindrical 3D culture s. However, during operation (for instance, when changing the cell medium and when rinsing), the cells may easily slip out of the cell culture well, which will result in the loss of experimental data and burden on the operator.

In addition, high-throughput experimental technology enables efficient screening on identifying drug target in biomedical research, so that a 3D cell culture device which can be applied to high-throughput analysis is desirable. In addition, a device in high-throughput format will also make long-term tracking easier. Therefore, how the cell culture device can be made for 3D culture, reduce cell loss, and how the operation for high-throughput analysis and long-term tracking can be made more convenient through structural design improvement, is an important issue yet to be solved in this field.

SUMMARY OF THE DISCLOSURE

In response to the above-referenced technical inadequacies, the present disclosure provides a microwell device array, which can be applied to 3D cell culture, effectively prevents cells from flowing out of the cell culture well, and can provide for long-term study and high-throughput analysis of isolated single cells.

In one aspect, the present disclosure provides a microwell device that includes a substrate and a plurality of microwells formed on the substrate. In addition, each of the microwells includes a cavity being recessed on the substrate and an opening, and the diameter of the opening is smaller than the largest inner diameter of the cavity. Furthermore, the microwells are curved. Preferably, the microwells are negatively curved.

In certain embodiments, the material of the substrate is selected from the group consisting of poly(acrylamide), polydimethylsiloxane, poly(lactic-co-glycolic acid), gelatin, silicone, polydimethylsiloxane, polyethylene, polystyrene, polyolefin, polyolefin copolymers, polycarbonate, ethylene vinyl acetate, polypropylene, polysulfone, polytetrafluoroethylene (PTFE), compatible fluoropolymer, poly(styrene-butadiene-styrene), and combinations thereof.

In certain embodiments, the length of the substrate ranges from 10 mm to 30 mm, and the width of the substrate ranges from 10 mm to 30 mm.

In certain embodiments, the number of the microwells is greater than or equal to 100.

In certain embodiments, the spacing between adjacent ones of the microwells is uniform or non-uniform.

In certain embodiments, the shape of each of the microwells is spherical or ellipsoidal.

In certain embodiments, the diameter of the opening ranges from 26 μm to 155 μm.

In certain embodiments, the largest inner diameter of the cavity ranges from 40 μm to 215 μm.

In certain embodiments, each of the microwells has a side surface and a bottom surface, and wherein the curvatures of the side surface and the bottom surface are not 0.

In certain embodiments, the side surface and the bottom surface have different curvatures or the same curvature. In certain embodiments, the microwell device further includes a functional coating layer being coated on the inner surface of at least one of the plurality of microwells but not on the surface of the flat substrate.

In certain embodiments, the microwell device further includes a functional coating layer being coated on the surfaces of both a top surface of the substrate and the inner surface the microwells.

In certain embodiments, the microwell device further includes a lid having a functional layer on a surface of the lid, and wherein the lid is detachably covered onto the microwell device.

In certain embodiments, the material of the functional coating layer is selected from the group consisting of extracellular matrix proteins, glycosaminoglycan, polypeptide, proteoglycan, aminoglycan, and polysaccharide protein.

In certain embodiments, the material of the functional coating layer and the functional layer are selected from the group consisting of extracellular matrix proteins, glycosaminoglycan, polypeptide, proteoglycan, aminoglycan, and polysaccharide protein.

In certain embodiments, the plurality of microwells are in at least two different sizes.

In another aspect, the present disclosure provides a method for manufacturing a microwell device, which includes the following steps. Firstly, a microcolumn array having a plurality of microcolumns is produced from a first template by photolithography or soft lithography. Next, after a lift-off layer is coated on the microcolumn array, a plurality of glass microspheres are disposed on each of the plurality of the microcolumns of the microcolumn array. Further, silicon is poured onto the microcolumn array being disposed with the glass microspheres, the silicone is cured, and then the cured silicone is separated from the microcolumn array and the glass microspheres to form a second template having a plurality of microcavities. After that, epoxy material is poured onto the second template, the epoxy material is cured, and then the cured epoxy material is separated from the second template to form a device mold. Lastly, a mold material is poured onto the microwell device mold, the mold material is cured, and then the cured mold material is separated from the microwell device mold to obtain the microwell device.

In certain embodiments, the depth of each of the microcolumns is shallower than 45 μm.

In certain embodiments, the material of the lift-off layer is protein.

One of the advantages of the present disclosure is that, the microwell device and the method of manufacturing the same of the present disclosure can make the cells experiencing 3D microenvironment, reduce cell loss, and make it easy for the experimenters to operate through the technical solution of "each of the microwells includes a cavity being recessed on the substrate and an opening, and wherein the diameter of the opening is smaller than the largest inner diameter of the cavity" and "the plurality of microwells are curved".

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 1:
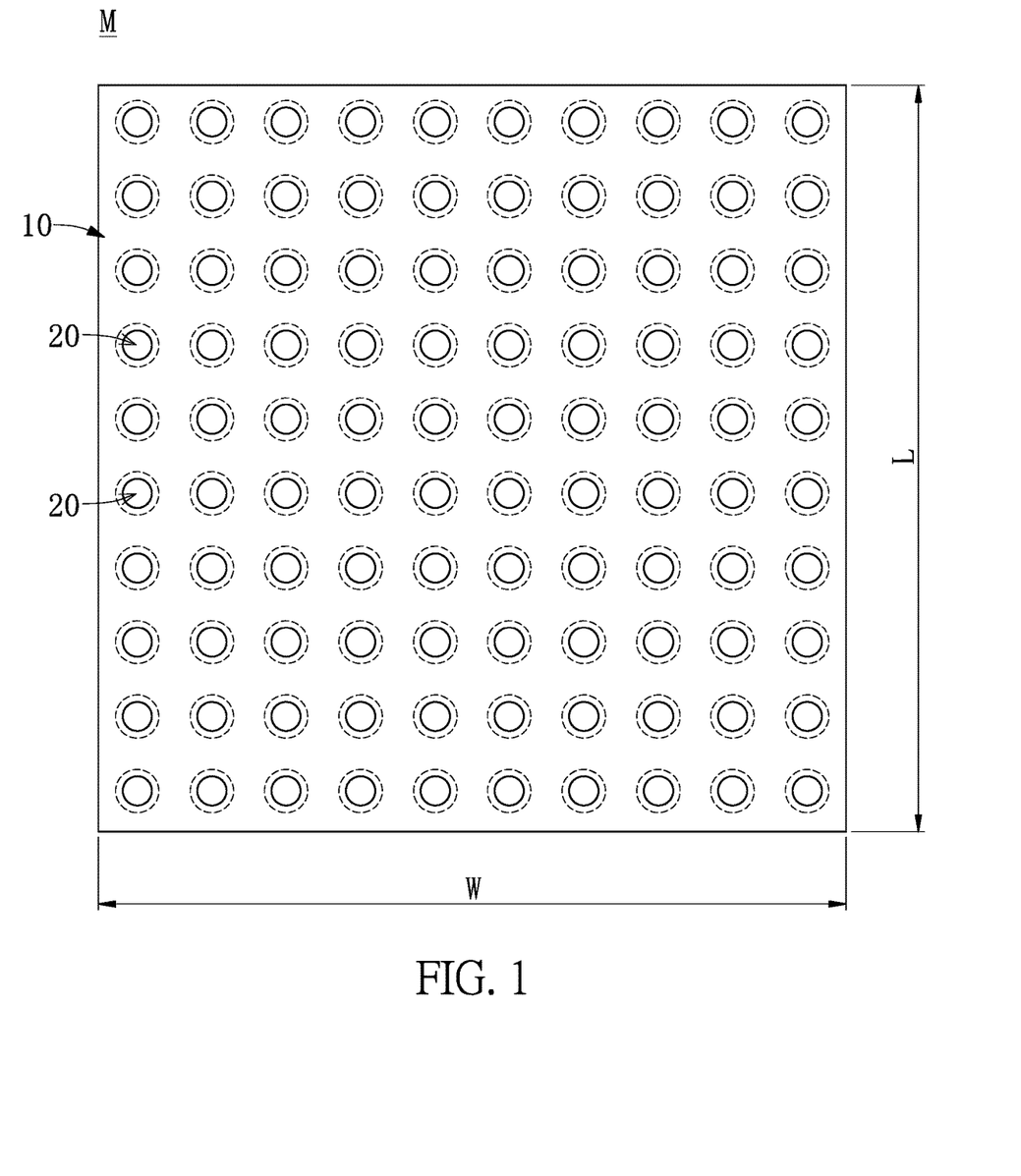
FIG. 1 is a top view of a microwell device according to a first embodiment of the present disclosure.
Figure 2:
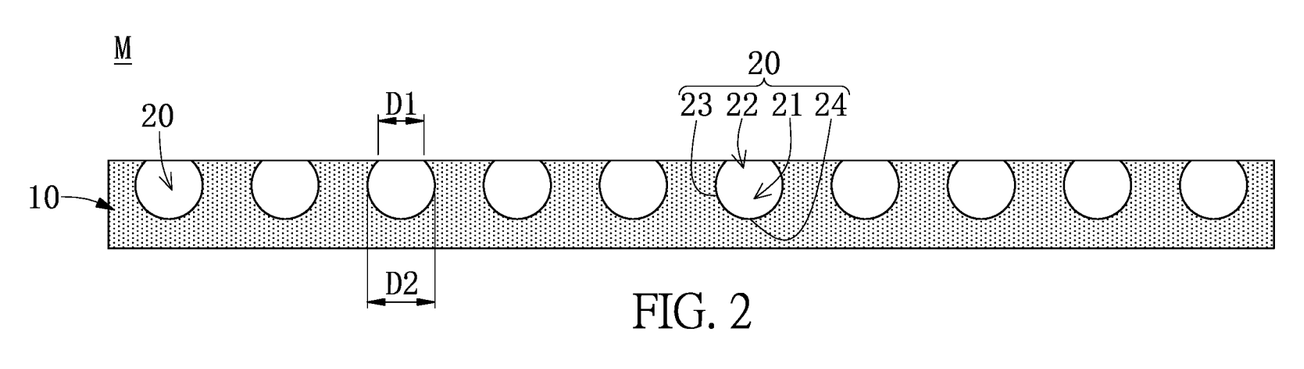
FIG. 2 is a cross-sectional view of the microwell device according to the first embodiment of the present disclosure.

Referring to FIG. 1 to FIG. 2, a first embodiment of the present disclosure provides a microwell device M including a substrate 10 and a plurality of microwells 20 formed on the substrate 10. Each of the microwells 20 includes a cavity 21 being recessed on the substrate 10 and an opening 22, and wherein the diameter D1 of the opening 22 is smaller than the largest inner diameter D2 of the cavity 21. In addition, the plurality of microwells 20 are curved.

Further, the material of the substrate 10 can, but not limited to being, poly(acrylamide), polydimethylsiloxane, poly(lactic-co-glycolic acid), gelatin, silicone, polydimethylsiloxane, polyethylene, polystyrene, polyolefin, polyolefin copolymers, polycarbonate, ethylene vinyl acetate, polypropylene, polysulfone, polytetrafluoroethylene (PTFE), compatible fluoropolymer, or poly(styrene-butadiene-styrene).

Referring to FIG. 1, the length L of the substrate 10 of the device M of the present disclosure can be 10 mm to 30 mm, and the width W of the substrate 10 can be 10 mm to 30 mm, but is not limited thereto. Further, the spacing between adjacent ones of the microwells 20 can be uniform or non-uniform, and the number of the microwells 20 can be greater than or equal to 100. In other embodiments, the substrate of the microwell device of the present disclosure can be disc-shaped, oval-shaped, or a polygon from the top view.

Figure 3:
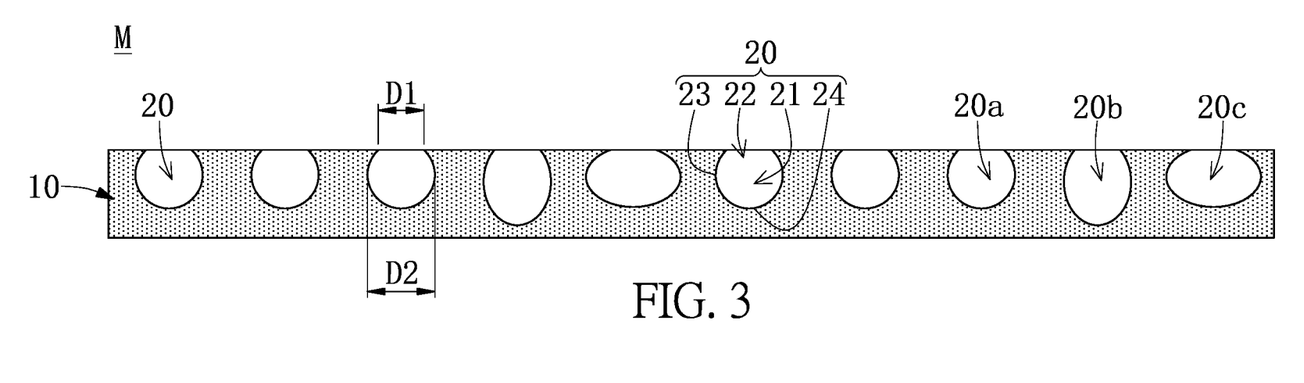
FIG. 3 is another cross-sectional view of the microwell device of the present disclosure.

Referring to FIG. 2 and FIG. 3, the shape of each of the microwells 20 can be spherical 20a or ellipsoidal 20b, 20c. Preferably, the ratio of the diameter D1 of the opening 22 of the microwell 20 to the largest inner diameter D2 of the cavity 21 of the microwell 20 is from 1:0.13 to 1:0.97. More preferably, the ratio of the diameter D1 of the opening 22 of the microwell 20 to the largest inner diameter D2 of the cavity 21 of the microwell 20 is from 1:0.43 to 1:0.66. Therefore, during cell culture, a single cell can be seeded into each microwell 20 separately, and the opening 22 which is narrower than the cavity 21 can effectively prevent the cells from sliding out of the microwell 20.

Specifically speaking, the diameter D1 of the opening 22 ranges from 26 μm to 155 μm, and the largest inner diameter D2 of the cavity 21 ranges from 40 μm to 215 μm, but is not limited thereto. Each of the microwells 20 includes a side surface 23 and a bottom surface 24, the curvatures of the side surface 23 and the bottom surface 24 are not 0, and the side surface 23 and the bottom surface 24 have different curvatures or the same curvature. In addition, at least two of the microwells 20 can have different sizes.

Figure 4:
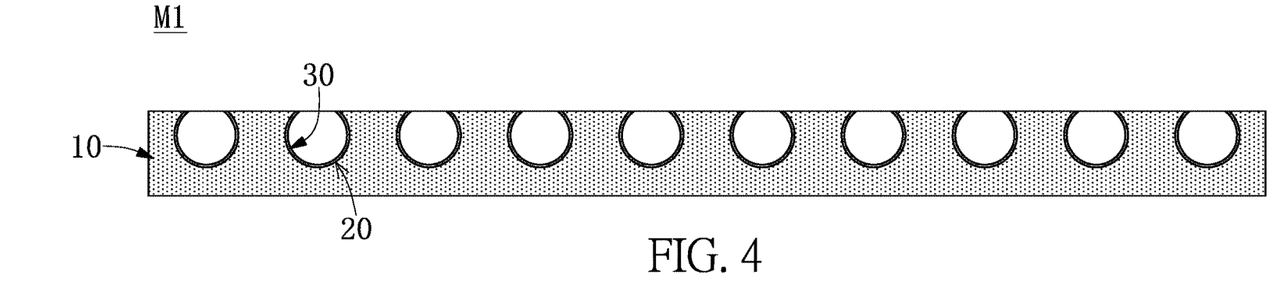
FIG. 4 is a cross-sectional view of the microwell device M1 of the present disclosure.
Figure 5:
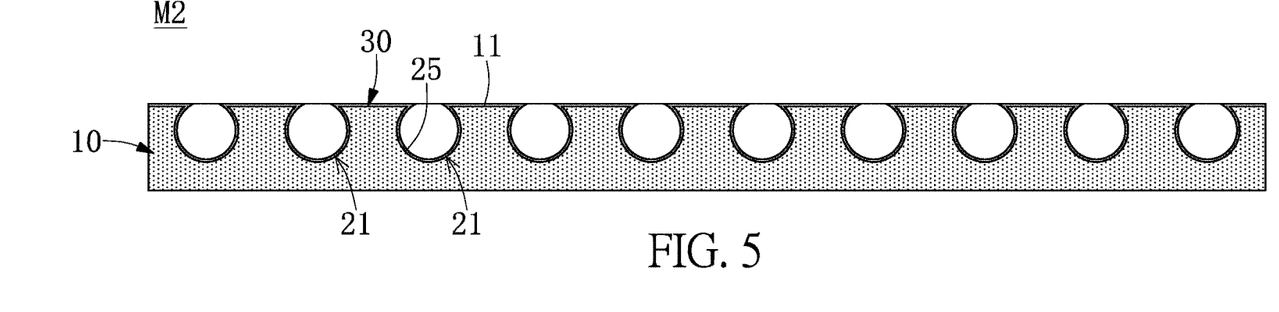
FIG. 5 is a cross-sectional view of the microwell device M2 of the present disclosure.
Figure 6:
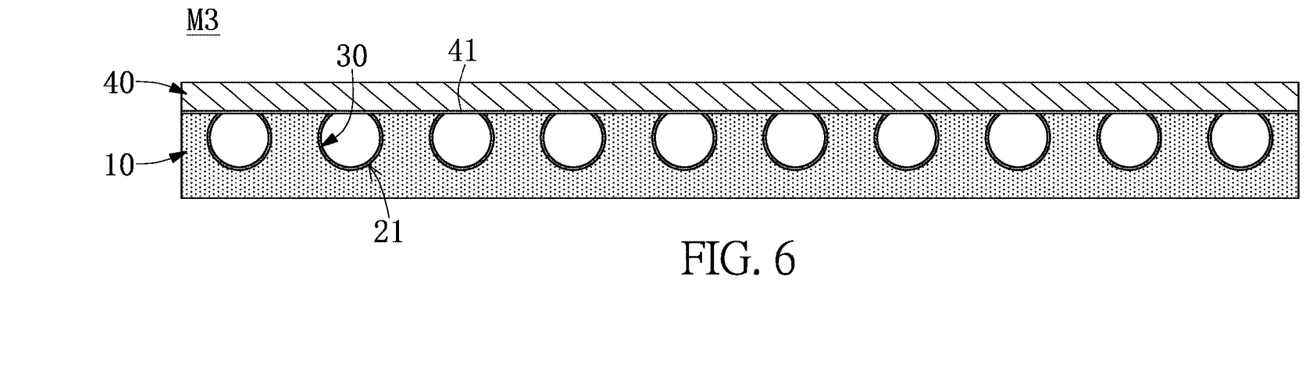
FIG. 6 is a cross-sectional view of the microwell device M3 of the present disclosure.
Figure 7:
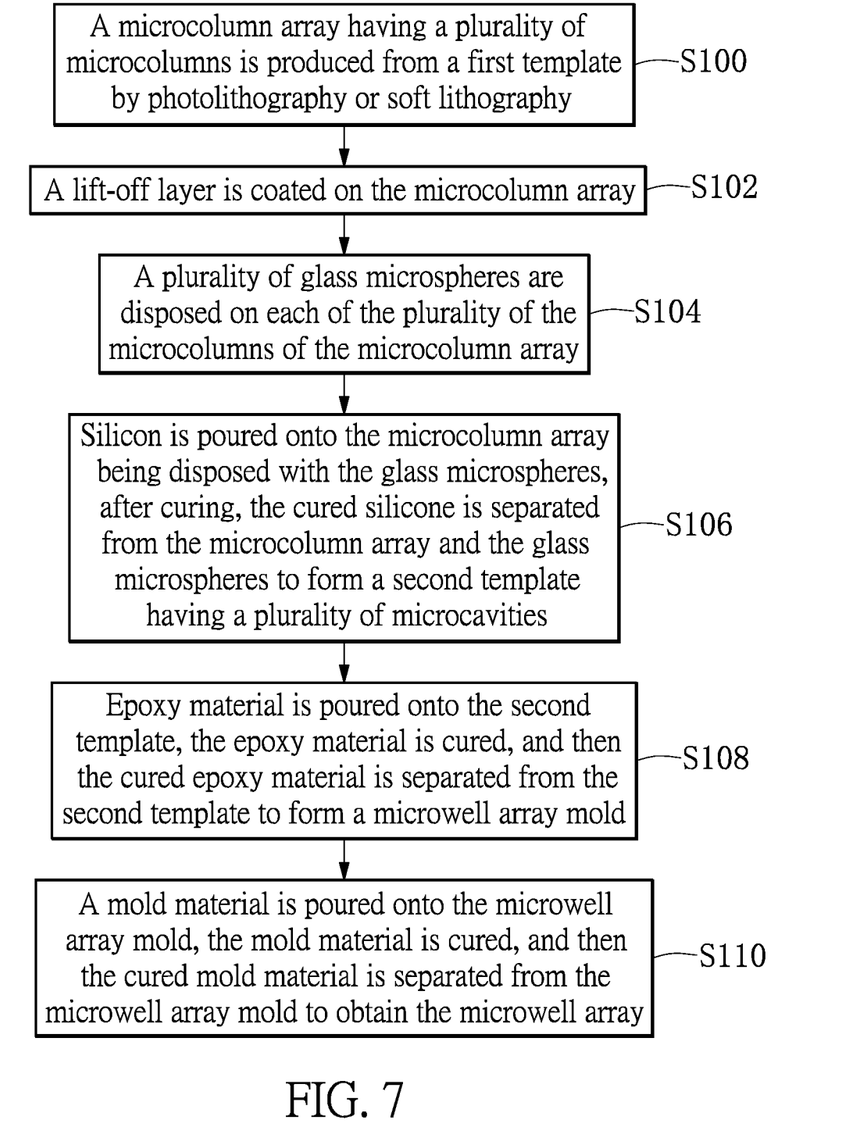
FIG. 7 is a flow chart of a method for manufacturing the microwell device according to a second embodiment of the present disclosure.
Figure 8:
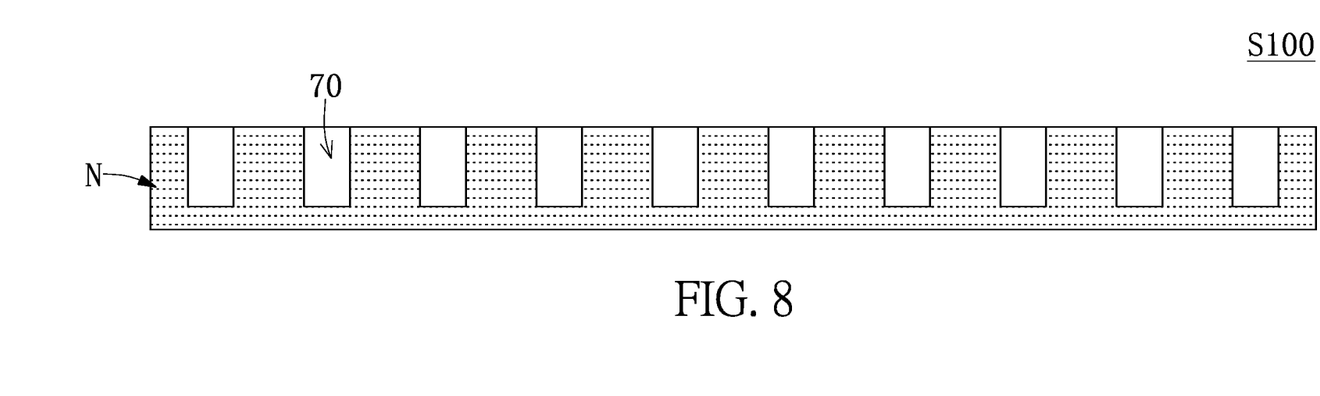
FIG. 8 is a schematic view of step S100 of the method for manufacturing the microwell device according to the second embodiment of the present disclosure.
Figure 9:
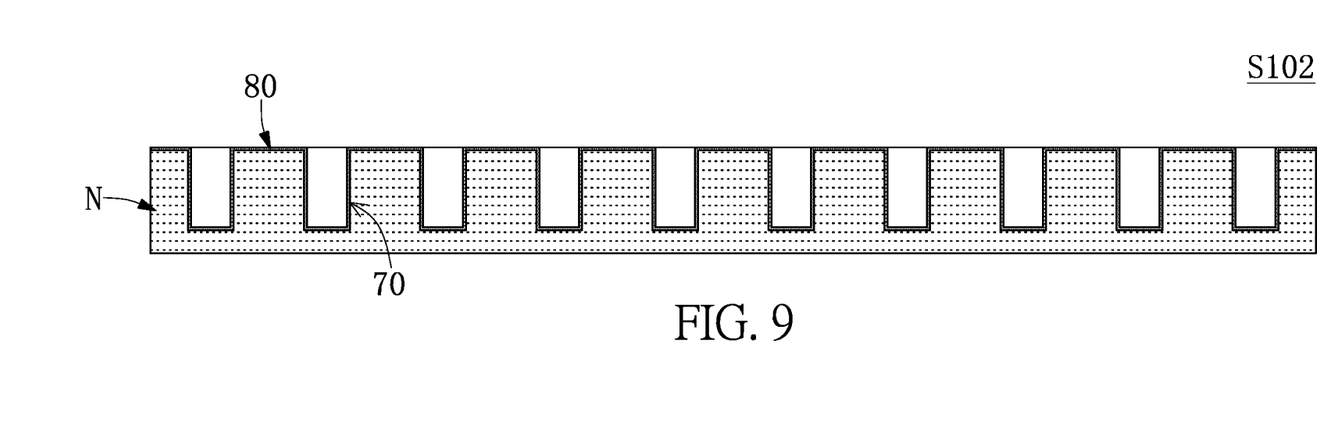
FIG. 9 is a schematic view of step S102 of the method for manufacturing the microwell device according to the second embodiment of the present disclosure.

Referring to FIG. 2, the microwell device M with no coating (conjugation) can be called a "bare substrate". Referring to FIG. 4, in other embodiments, the device M1 can further include a functional coating layer 30 being coated only on the surface of at least one of the microwells 20, and the functional coating layer 30 can to selected from the group consisting of glycosaminoglycan, polypeptide, proteoglycan, aminoglycan, and polysaccharide protein, refer to as "isolated s". Referring to FIG. 5, in other embodiments, the functional coating layer 30 of the microwell device M2 can be coated on the surfaces the top surface 11 of the substrate 10 and the inner surface 25 of each of the cavity 21 of the microwells 20, referred to as an "all-coated substrate". Referring to FIG. 6, in other embodiments, the microwell device M3 can further include a lid 40 having a functional layer 41 on the surface of the lid 40, and the lid 40 is detachably covered onto the microwell device M3 which the microwells 20 with the functional coating layer 30, and referred to as "closed s". In addition, the material of the lid 40 is same as the substrate 10 thereof, and the material of the functional layer 41 of the lid 40 is same as the functional coating layer 30 thereof.

Second Embodiment

Referring to FIG. 7 to FIG. 13, a second embodiment of the present disclosure provides a method for manufacturing a microwell device M, which at least includes step S100 to step S110. Firstly, in step S100, a microcolumn array N having a plurality of microcolumns 70 is produced from a first template by photolithography or soft lithography. In addition, the microcolumn array N can be made of polydimethylsiloxane (PDMS). In step S102, after a lift-off layer 80 [1% bovine serum albumin (BSA) in phosphate-buffered saline (PBS)] is coated on the microcolumns array N, a plurality of glass microspheres 90 are disposed on each of the plurality of the microcolumns 70 of the microcolumn array N (step S104). Next, in step S106, silicon (fast-curing silicone) is poured onto the microcolumn array N being disposed with the glass microspheres 90, after curing, the cured silicone is separated from the microcolumn array N and the glass microspheres 90 to form a second template K having a plurality of microcavities. After that, in step S108, epoxy material (two-part 5-min epoxy resin) is poured onto the second template K, the epoxy material is cured, and then the cured epoxy material is separated from the second template K to form a microwell device mold J. Lastly, in step S110, a mold material (polyacrylamide) is poured onto the microwell device mold J, the mold material is cured, and then the cured mold material is separated from the device mold J to obtain the microwell device M. It should be noted that, the microwell device M with no conjugation can be called a "bare substrate".

Figure 10:
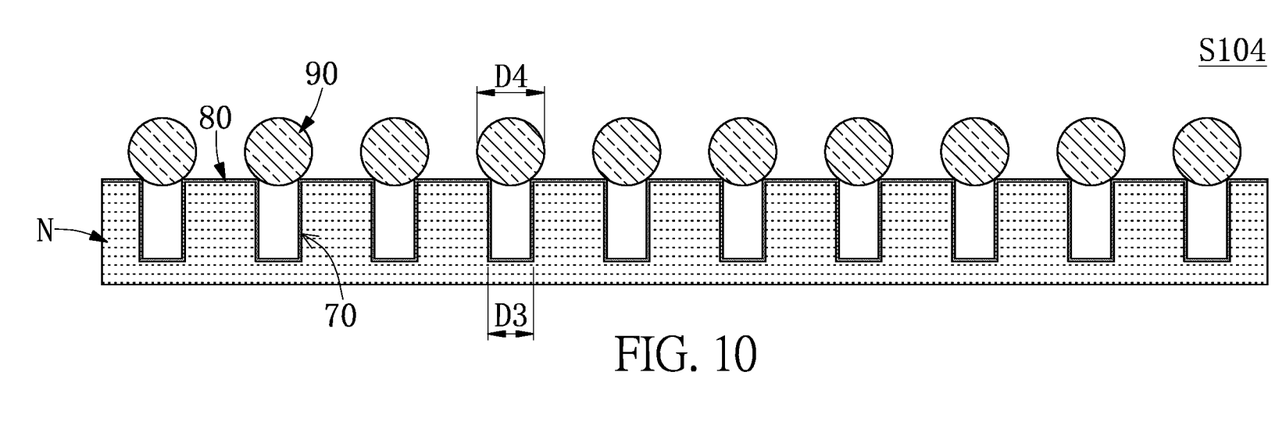
FIG. 10 is a schematic view of step S104 of the method for manufacturing the microwell device according to the second embodiment of the present disclosure.
Figure 11:
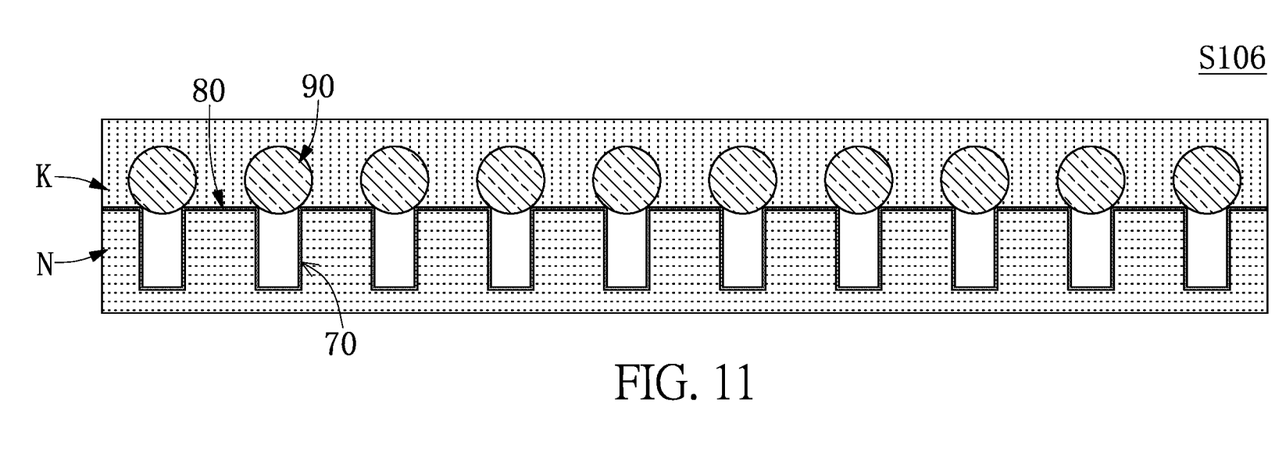
FIG. 11 is a schematic view of step S106 of the method for manufacturing the microwell device according to the second embodiment of the present disclosure.
Figure 12:
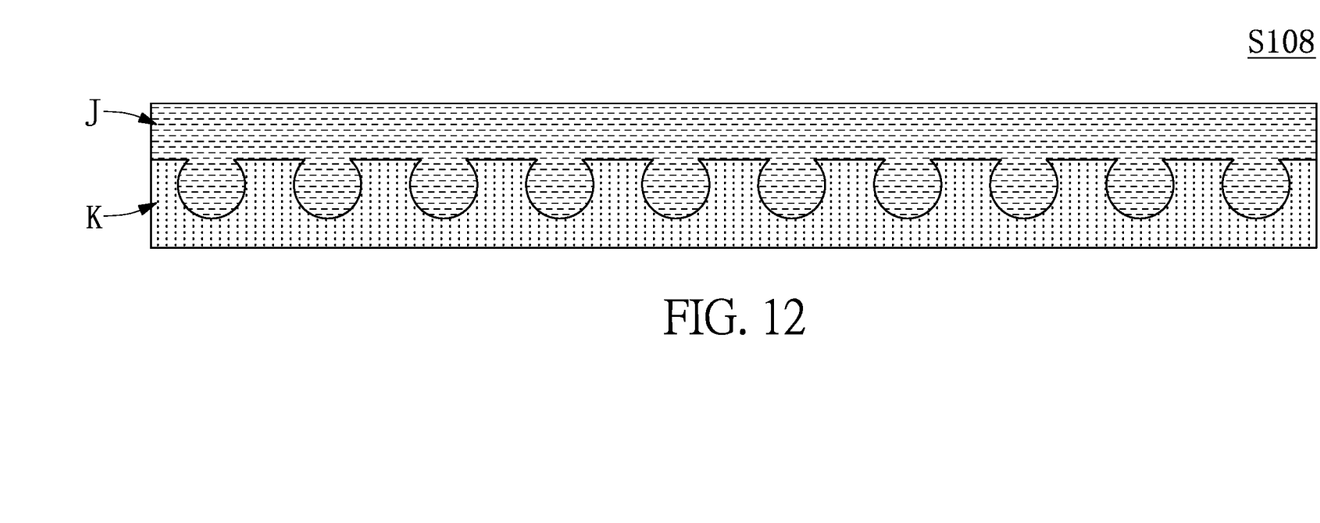
FIG. 12 is a schematic view of step S108 of the method for manufacturing the microwell device according to the second embodiment of the present disclosure.
Figure 13:
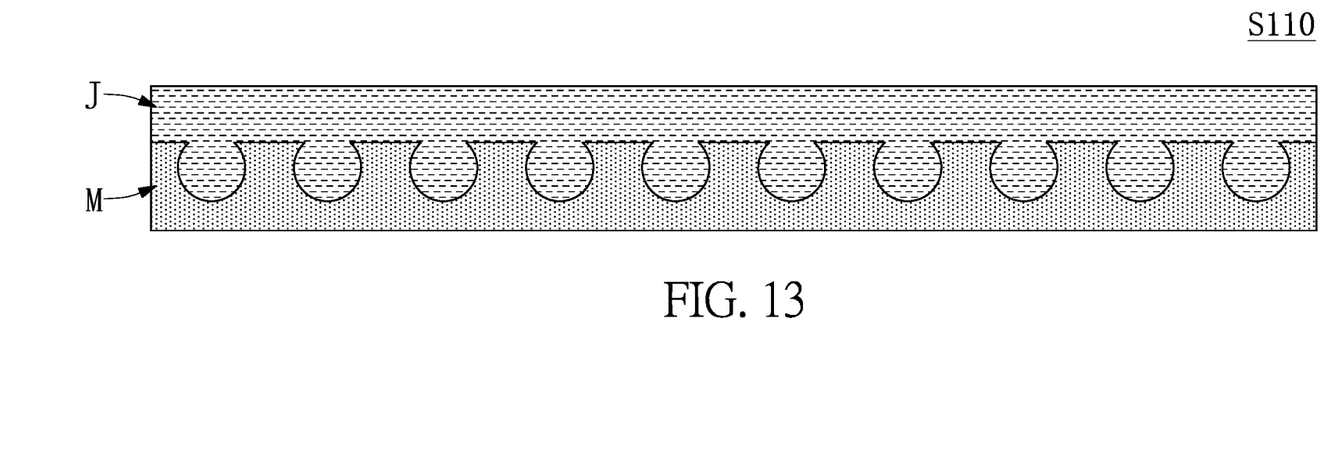
FIG. 13 is a schematic view of step S110 of the method for manufacturing the microwell device according to the second embodiment of the present disclosure.

Referring to FIG. 2 and FIG. 10, specifically speaking, the diameters D3 of the microcolumns 70 determine the diameters D1 of the openings 22 of the microwells 20 of the microwell device M. It is worth mentioning that, the diameters D4 of the glass microspheres 90 determine the largest inner diameter D2 of the cavities 21 of the microwells 20 of the microwell device M. In other embodiments, the depth of each of the plurality of microcolumns is 45 μm, and the glass microspheres 90 of diameters (D3)=40, 60, 80, 100, and 200 μm are placed into the diameters (D4)=26, 40, 53, 66, or 132 μm of microcolumns 70, respectively, and the final geometry is shown in Table 1. In addition, the mold material such as polyacrylamide can be slightly elongated along the Z axis.

TABLE 1

Summary of microwell and template geometry
(all units except ε are μm.)

| glass microspheres (D4) | the largest inner diameter (D2) | microcolumns diameter (D3) | the diameters of openings (D1) | elongation ε along the z axis |
|---|---|---|---|---|
| 40 | 41.0 ± 2.3 | 26 | 33.6 ± 4.0 | 1.13 ± 0.05 |
| 60 | 59.4 ± 3.8 | 40 | 46.1 ± 6.2 | 1.15 ± 0.04 |
| 80 | 80.3 ± 3.3 | 53 | 62.9 ± 6.6 | 1.14 ± 0.03 |
| 100 | 97.7 ± 3.6 | 66 | 78.0 ± 4.7 | 1.15 ± 0.08 |
| 200 | 204.7 ± 7.7 | 132 | 145.2 ± 8.1 | 1.16 ± 0.03 |

Preferably, the ratio of the diameter D3 of the microcolumns 70 to the diameter D4 of the glass microspheres 90 is from 1:0.13 to 1:0.97. More preferably, the ratio of the diameter D3 of the microcolumns 70 to the diameter D4 of the glass microspheres 90 is from 1:0.43 to 1:0.66.

To culture cells with strong cell-matrix adhesions, the extracellular matrix (ECM) proteins such as collagen or fibronectin is conjugated to the substrate and/or the microwells by using the bifunctional crosslinker sulfo-SANPAH, as the functional coating layer (and the functional layer of the lid).

Third Embodiment

Figure 14:
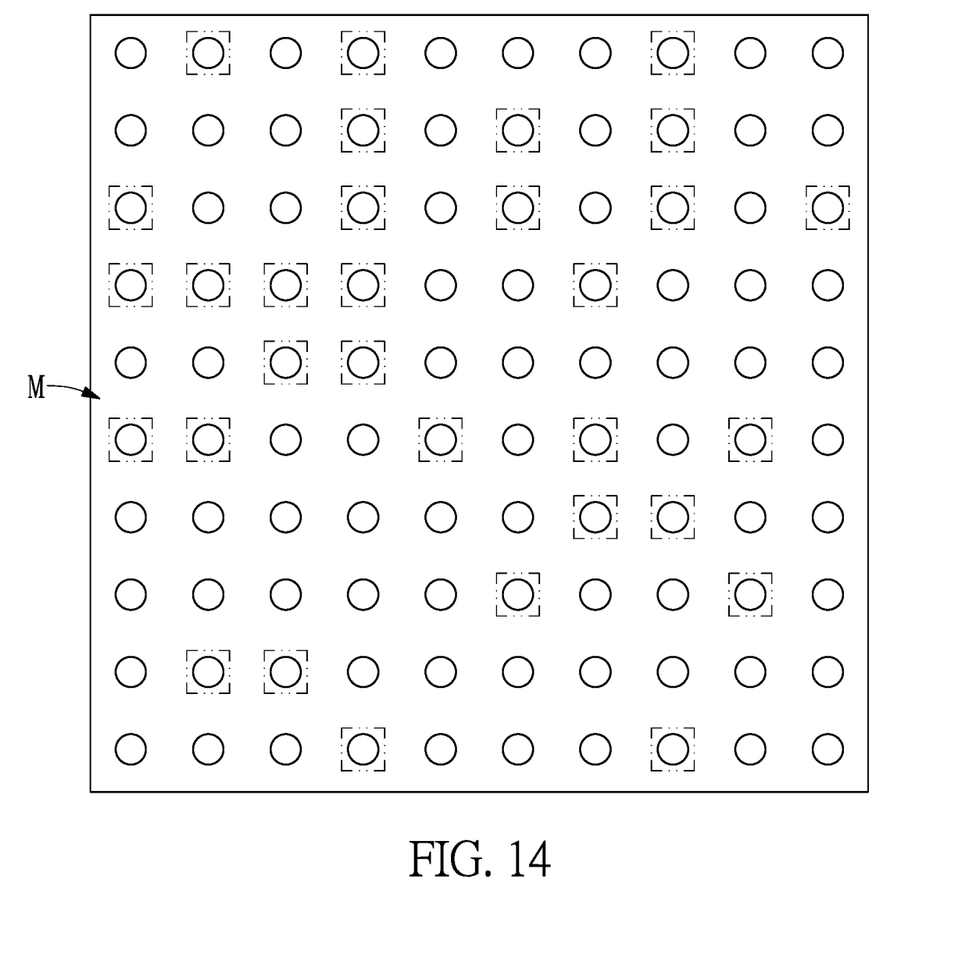
FIG. 14 is a schematic view from the result culturing 80 μm microwell substrates containing MDCK cells after step (1) of a third embodiment of the present disclosure.
Figure 15:
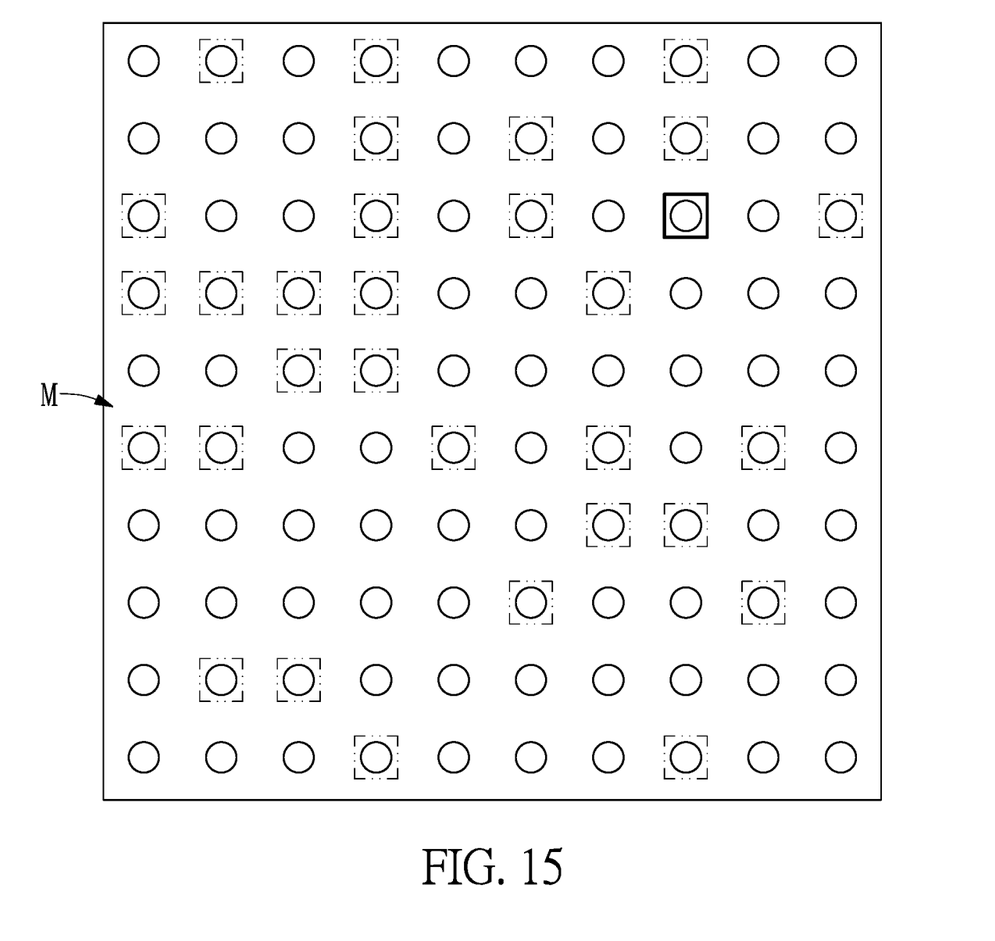
FIG. 15 is a schematic view from the result culturing 80 μm microwell substrates containing MDCK cells after step (4) of a third embodiment of the present disclosure.

The Madin-Darby canine kidney (MDCK) cells were cultured in the s of the microwell device (80 µm of the largest inner diameter) on an orbital shaker. The microwell device was perturbed sequentially using four 30 minutes sessions using different parameters: (1) at 100 rpm with s facing upward; (2) at 100 rpm with microwells facing downward; (3) at 200 rpm with microwells facing upward; and (4) at 200 rpm with microwells facing downward. Results from after step (1) and (4) are shown in FIG. 14 and FIG. 15, respectively. Over the 2 hours perturbation, only one microwell of MDCK cell (black border in FIG. 15) was lost out of 32 microwells (dashed box in FIGS. 14 and 15). Therefore, this embodiment shows that the microwells of the microwell device of the present disclosure can prevent cells from slipping out of the microwells.

Fourth Embodiment

Figure 16:
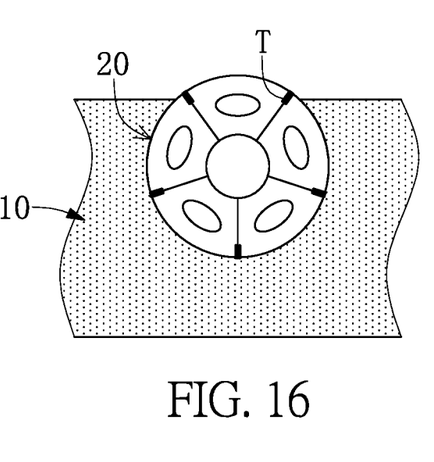
FIG. 16 is a schematic view of MDCK cells in a "bare substrate" 60 μm in diameter, after 4 days of culture.
Figure 17:
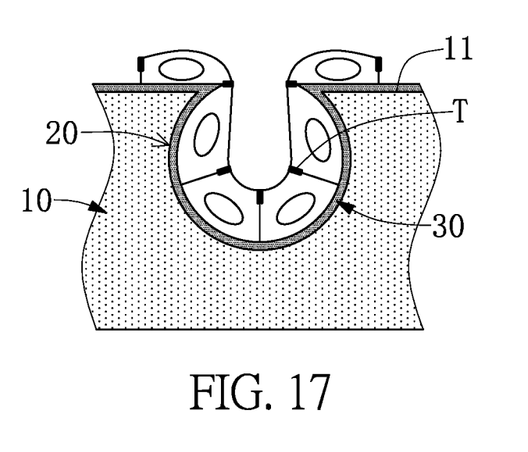
FIG. 17 is a schematic view of MDCK cells in an "all-conjugated substrate" 60 μm in diameter, after 6 days of culture.
Figure 18:
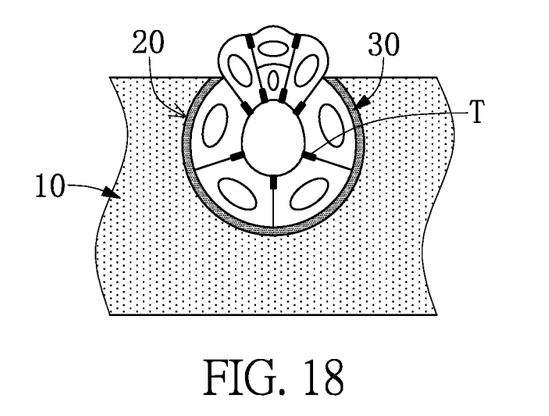
FIG. 18 is a schematic view of MDCK cells in an "isolated microwell" 60 μm in diameter, after 7 days of culture.
Figure 19:
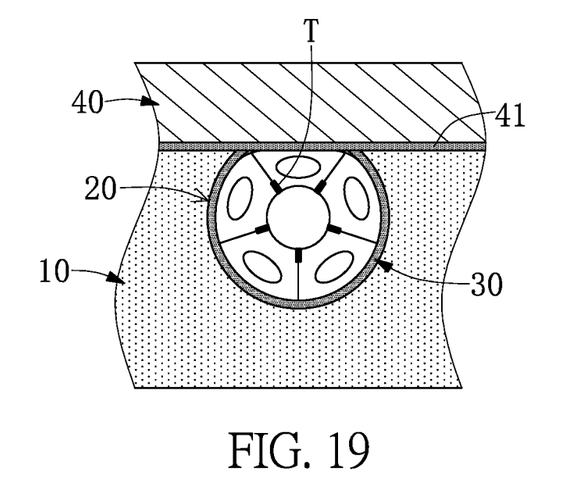
FIG. 19 is a schematic view of MDCK cells in a "closed micowells" 40 μm in diameter, after 7 days of culture.

Epithelial cells were cultured on the microwell device conjugated with ECM proteins (the functional layer 30) under four scenarios: a bare substrate (no conjugation), an all-coated substrate (ECM proteins everywhere), isolated microwells (only walls conjugated), and closed microwells (thin conjugated lids). On bare substrate, MDCK cells did not adhere to the substrate 10 nor the microwell 20 and exhibited an inverted polarity, with tight junctions T facing outward (as shown in FIG. 16), as reported when MDCK cells were cultured in suspension. On the all-coated substrate, MDCK cells covered the microwell 20 and top surface 11 of the substrate 10 over time, with the tight junctions T facing the culture medium (as shown in FIG. 17). In isolated microwells, cells grew and divided on the microwell 20, with the population of daughter cells eventually growing out of the microwell 20 (as shown in FIG. 18). In closed microwells, MDCK cells had their tight junctions T facing the lumen (as shown in FIG. 19), which is the same polarity as cysts grown in 3D gel in the related literature. Therefore, this embodiment shows that the coating position of the functional coating layer 30 (ECM proteins) will affect organization of cell aggregates.

Fifth Embodiment

Figure 20:
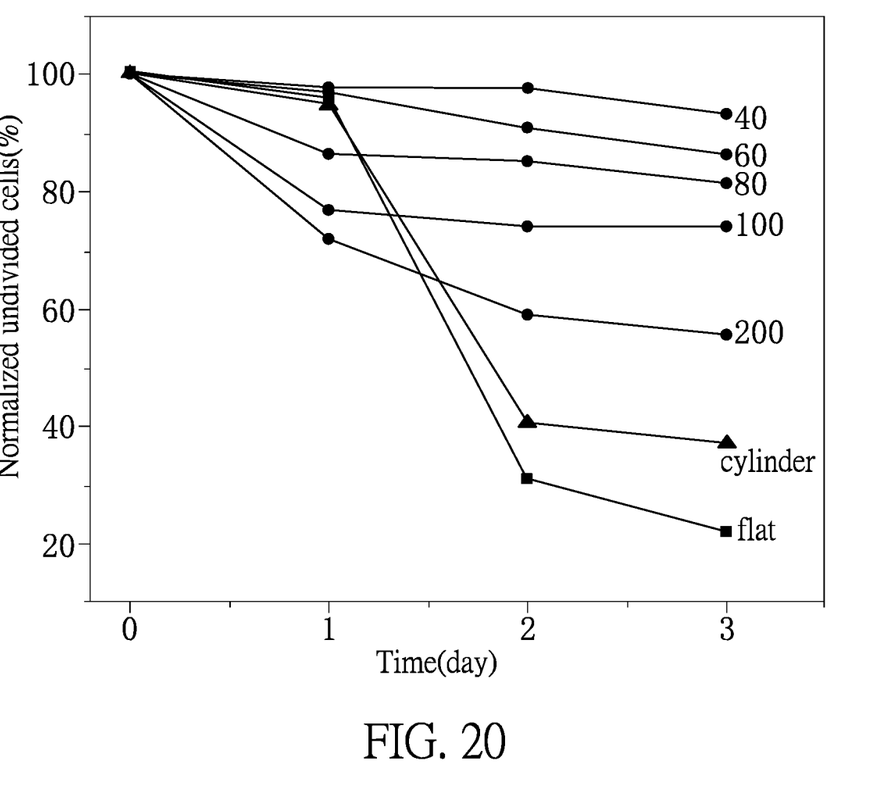
FIG. 20 is a scatter plots of percentages of undivided cell-tracking data from the microwell device with different diameters (the largest inner diameters=40, 60, 80, 100, 200 μm), 2D cultures (a flat culture device), and cylindrical microwells.

In addition to epithelial cells, fibroblasts were cultured in the device of the present disclosure. When cultured on "all-coated substrates", fibroblasts tend to migrate to the flat substrate (data not shown). When cultured in "isolated microwells", fibroblasts exhibited cell-cycle arrest. G1-synchronized REF52 cells were seeded into microwells 40, 60, 80, 100, or 200 µm in diameter, as well as on control planar substrate and cylindrical s of 90 µm in diameter and tracked cell division every day for 3 days. Referring to FIG. 20, on day 3, it is clear to see that the greater the ratio of substrate curvatures, the less division occurs in the cells. The division rate of cells in cylindrical wells is between the division rate of cells grown on a flat culture device and that of cells grown in spherical s, but closer to the cells on the flat substrate. The bottom of the cylindrical is still flat and the adhesions of cells on attaching to the bottom part are coplanar and thus cells may still sense and respond to the partial 2D microenvironment. In other words, the flat bottom of the cylindrical well may have affected cellular behaviors more than the curved wall. Some cells start to divide one day after seeding in 80, 100, and 200 µm microwells, but most cells do not divide in the first day even on the flat control and cylindrical well. Therefore, this embodiment shows that cell proliferation can be controlled through a well-defined geometric microenvironment in 3D cell culture device, which is never shown before.

One of the advantages of the present disclosure is that, the device and the method of manufacturing the same of the present disclosure can make the cell culture device closer reflect the growth environment of cells in vivo, reduce cell loss, and make it easy for the experimenters to operate through the technical solution of "each of the microwells includes a cavity being recessed on the substrate and an opening, and wherein the diameter of the opening is smaller than the largest inner diameter of the cavity" and "the plurality of microwells are curved".

In addition, having the design of 3D cell culture compatible with the high-throughput screening is important for the application in drug screening where there are large compound libraries. Therefore, arranging the microwells into arrays can increase the throughput of analysis at the single well resolution and also makes the long-term tracking more easily.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A microwell device, comprising:
   a substrate; and
   a plurality of microwells formed on the substrate, each of the microwells including a cavity being recessed on the substrate and an opening, and wherein a diameter of the opening is smaller than a largest inner diameter of the cavity and the largest inner diameter of the cavity ranges from 38.7 µm to 83.6 µm;
   wherein the plurality of microwells are curved, and the diameter of the opening ranges from 26 µm to 56.3 µm.

2. The microwell device according to claim 1, wherein the substrate is selected from the group consisting of poly (acrylamide), polydimethylsiloxane, poly(lactic-co-glycolic acid), gelatin, silicone, polydimethylsiloxane, polyethylene, polystyrene, polyolefin, polyolefin copolymers, polycarbonate, ethylene vinyl acetate, polypropylene, polysulfone, polytetrafluoroethylene (PTFE), compatible fluoropolymer, poly(styrene-butadiene-styrene), and combinations thereof.

3. The microwell device according to claim 1, wherein a length of the substrate ranges from 10 mm to 30 mm, and a width of the substrate ranges from 10 mm to 30 mm.

4. The microwell device according to claim 1, wherein a number of the microwells is greater than or equal to 100.

5. The microwell device according to claim 1, wherein a spacing between adjacent ones of the microwells is uniform or non-uniform.

6. The microwell device according to claim 1, wherein a shape of each of the microwells is spherical or ellipsoidal.

7. The microwell device according to claim 1, wherein each of the microwells has a side surface and a bottom surface, and wherein the curvatures of the side surface and the bottom surface are not 0.

8. The microwell device according to claim 7, wherein the side surface and the bottom surface have different curvatures or the same curvature.

9. The microwell device according to claim 1, wherein the microwell device further includes a functional coating layer being coated on an inner surface of at least one of the plurality of microwells.

10. The microwell device according to claim 1, wherein the microwell device further includes a functional coating layer being coated on the surfaces of both a top surface of the substrate and an inner surface of the s.

11. The microwell device according to claim 9, wherein the microwell device further includes a lid having a functional layer on a surface of the lid, and wherein the lid is detachably covered onto the microwell device.

12. The microwell device according to claim 9, wherein the functional coating layer is selected from the group consisting of extracellular matrix proteins, glycosaminoglycan, polypeptide, proteoglycan, aminoglycan, and polysaccharide protein.

13. The microwell device according to claim 10, wherein the functional coating layer is selected from the group consisting of extracellular matrix proteins, glycosaminoglycan, polypeptide, proteoglycan, aminoglycan, and polysaccharide protein.

14. The microwell device according to claim 11, wherein the functional coating layer and the functional layer are selected from the group consisting of extracellular matrix proteins, glycosaminoglycan, polypeptide, proteoglycan, aminoglycan, and polysaccharide protein.

15. The microwell device according to claim 1, wherein the plurality of microwells are in at least two different sizes.

16. A method for manufacturing a microwell device, comprising:
(a) producing a microcolumn array from a first template by photolithography or soft lithography, wherein the microcolumn array includes a plurality of microcolumns;
(b) coating a lift-off layer on the microcolumn array;
(c) disposing a plurality of glass microspheres on each of the plurality of the microcolumns of the microcolumn array;
(d) pouring silicone onto the microcolumn array disposed with the glass microspheres, then curing the silicone, and then separating the cured silicone from the microcolumn array and the glass microspheres to form a second template having a plurality of microcavities,
(e) pouring an epoxy material onto the second template, then curing the epoxy material, and then separating the cured epoxy material from the second template to form a microwell device mold; and
(f) pouring a mold material onto the microwell device mold, then curing the mold material, and then separating the cured mold material from the microwell device mold to obtain the microwell device.

17. The method according to claim 16, wherein the depth of each of the microcolumns is shallower than 45 μm.

18. The method according to claim 16, wherein the lift-off layer is protein.

* * * * *